(12) United States Patent
Wessels et al.

(10) Patent No.: US 6,314,312 B1
(45) Date of Patent: Nov. 6, 2001

(54) METHOD AND SYSTEM FOR DETERMINING MOVEMENT OF AN ORGAN OR THERAPY REGION OF A PATIENT

(75) Inventors: Gerd Wessels, Effeltrich; Hubertus Feussner, Munich, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/537,280

(22) Filed: Mar. 29, 2000

(30) Foreign Application Priority Data

Mar. 30, 1999 (DE) .............................. 199 14 455

(51) Int. Cl.[7] ...................................... A61B 6/00
(52) U.S. Cl. ................ 600/427; 606/130; 600/429; 600/439
(58) Field of Search .................. 600/420, 424, 600/425, 426, 427, 431, 437, 439; 606/130; 378/69

(56) References Cited

U.S. PATENT DOCUMENTS 5,207,223 * 5/1993 Adler .
5,977,769 11/1999 Börnert et al. .
6,110,112 * 8/2000 Heywang-Koebrunner .
6,144,875 * 11/2000 Schweikard et al. .

FOREIGN PATENT DOCUMENTS

OS 197 51 761   10/1998 (DE) .
PS 198 09 460   9/1999 (DE) .

* cited by examiner

*Primary Examiner*—Marvin M. Lateef
*Assistant Examiner*—Runa Shah Qaderi
(74) *Attorney, Agent, or Firm*—Schiff Hardin & Waite (57) ABSTRACT

In a navigation system and method, sensors at location-invariant points are used to define a coordinate system serves for identifying the motion of an organ. An image of the organ can be registered in parallel therewith, by selection of a point whose path in the coordinate system is identified and displayed, for which purpose the image plane attitude is also identified and displayed by acquisition of a further sensor. Alternatively, a sensor can be attached to the organ, this position thereof being identified and the motion path being determined therefrom. A sensor located at an instrument is acquired in parallel therewith. The position of the instrument in the coordinate system is identified and displayed. The instrument can be manually or automatically moved.

51 Claims, 4 Drawing Sheets

METHOD AND SYSTEM FOR DETERMINING MOVEMENT OF AN ORGAN OR THERAPY REGION OF A PATIENT

BACKGROUND OF THE INVENTION

1. Field of the Invention

The present invention is directed to a method and a system for determining movement of a body organ or therapy region of a patient.

2. Description of the Prior Art

Minimally invasive therapies are increasingly gaining in significance. The goal of such systems is to keep the intervention into the body, and thus the stress on the patient, as slight as possible. Although minimally invasive therapies for location-invariant body regions or organs, for example in the field of neurosurgery or orthopedics, are already being widely employed, the use thereof for, for example, procedures directed to a specified site (for example, a biopsy) at moving organs presents problems. In contrast to manipulation at non-moving body regions, the therapist working in minimally invasive fashion must account for moving therapy regions, for example in the abdominal area, produced, for example, by respiration, blood pulsing, or peristaltic action. In order to exactly align one or more instruments (for example, laparoscope or needles) to a desired target region, for example a metastasis in the liver, and in order also to maintain this alignment during the movement of the organ, a continuous acquisition of the movement of the organ is required.

German PS 198 09 460 discloses a medical aiming device for respiration-adapted puncturing of a target that cannot be displayed with ultrasound using a centesis instrument that is connected to an ultrasound applicator. This aiming device is arranged so as to be longitudinally displaceable at a patient bed of a magnetic resonance apparatus. The centesis instrument can be aligned with respect to the target region on the basis of images of the examination subject registered with an ultrasound applicator as well as with the magnetic resonance apparatus. German OS 197 51 761 and German OS 196 07 023 disclose other systems for movement-adapted assistance in medical procedures.

SUMMARY OF THE INVENTION

An object of the present invention is to provide a method and a system that enable an adequately precise acquisition of the movement of an organ or body region, so that a therapist or operator is provided with exact knowledge with respect to the position of the organ or therapy region of interest.

This object is achieved in a method for determining the movement of an organ or therapy region of a patient having the following steps.

A navigation system having a number of sensors is employed to define a patient-specific coordinate system with one or more of the sensors at the patient at or in the region of location-invariant body parts. The position of at least one sensor that is essentially at rest relative to the moving organ or therapy region is identified within the coordinate system, the positional data thereof being employed for determining the attitude - in the coordinate system - of the image plane of an image of the moving organ or therapy region that is registered over time and reproduced at a monitor, or the attitude of the image plane is identified on the basis of the spatial position of the image registration system with respect to the patient. At least one point or section of the moving organ or therapy region within the image is defined and the motion-dependent path thereof is also identified and, based thereon, at least one point that is characteristic of the motion path is identified and displayed at a monitor within the coordinate system, which is also displayed on this monitor, together with the attitude of the image plane.

The monitor at which the point characteristic is displayed may be the same as the monitor on which the attitude of the image plane is continuously displayed, or may be a different monitor.

A navigation system for acquiring various sensor signals serves as basis for the inventive method. For example, active signal generators or reflectors can be employed as the sensors, the signals therefrom (generated or reflected) being acquired with a suitable acquisition unit. Such navigation systems are known in the field of medical applications. The coordinate system of the navigation system within which the position of the sensors is identified is individually defined for each patient on the basis of one or more location-invariant body parts. Regions close to bone such as, for example, the sternum, the upper iliac spur or the upper edge of the symphysis preferably serve for this purpose. The position of an essentially motionless sensor is acquired within this coordinate system, and the attitude of an image plane of an image of the moving organ or therapy region, that is isochronically registered with an image pickup method, is then determined based on the position of this substantially motionless sensor.

Alternatively, the identification of the plane can ensue on the basis of the spatial position of the image pickup system. The coordinate system as well as the attitude of the image plane are displayed at a monitor and simultaneously the registered image is displayed at the same or another monitor. In this way, the physician is informed where the image plane lies with reference to the patient-individual coordinate system; at the same time, he or she is provided with knowledge about the structure to be treated as a result of the registered, medical image. In order to then obtain information about the organ or region movement and in order to reproduce motion-referenced information in the coordinate system, the physician can particularly advantageously select a point or a region at the organ, for example, the edge of the liver, or in the region. This selection can be made, for example, directly at the image monitor that, for example, can be fashioned as a touch screen. A definition of the point or of the region of interest (ROI) is also possible using a cursor displayable at the monitor via a joystick. Thereafter, the position of this selected point is computationally determined in the coordinate system, and the movement of the selected point is likewise acquired. For example, either the entire motion path is then continuously displayed in the monitor at which the coordinate system is shown, or for example in the case of the liver, the respective reversing (extreme) points of the motion are displayed. The physician thus is provided with motion-referenced information correlated with the actual motion of the organ or of the region, which allows the physician to exactly determine the point-in-time at which the organ or the region is in the position displayed in the coordinate system.

According to an embodiment of the invention, the movement of at least one medical instrument, to be guided with respect to the organ or therapy region, is acquired in addition to the movement of the body organ or of the therapy region, and the position of the medical instrument, at which at least one sensor is arranged whose signal can be acquired with the navigation system, is likewise displayed at the monitor in the coordinate system.

After this, the attitude or spatial position of at least one medical instrument, for example a needle, is acquired with the navigation system. A sensor that enables the detection within the coordinate system is likewise located at the instrument. This position is also displayed at the monitor for the physician. He or she thus is provided with information as to the position and attitude of the instrument within the coordinate system as well as with respect to the image plane, and thus also with respect to the structure visually presented at the other monitor at which, for example, a metastasis can be seen. Based on the knowledge of the attitude of the metastasis or the like as well as the position of the medical instrument, this can then be guided exactly into the desired region despite the movement of the organ or region.

It has proven expedient to obtain an ultrasound image or an x-ray image as the image. The essentially motionless sensor in the former instance is arranged at an ultrasound applicator employed for the image pickup. The position of the ultrasound applicator defines the attitude of the image plane and this can be acquired without difficulty with the sensor located at the applicator. The ultrasound applicator can be applied to the patient in the inventive method at the exterior or it can be introduced into the patient via a small body opening and can be inserted to the moving organ or to the moving region. Care must be exercised in the positioning to ensure that the selected organ point or region (as is also true for the therapy region) does not migrate out of the image. In the case of an x-ray image exposure, the attitude of the image plane in the coordinate system is determined on the basis of the spatial position of the system components or of the central x-ray. The image plane preferably should proceed essentially in the direction of the longitudinal axis of the moving organ or region insofar such a longitudinal axis can be defined.

As described, the point or the section of the moving organ or region can be defined at the monitor, for example with a light pen or the like; the monitor can also be fashioned as touch screen monitor. Given knowledge of the relationships of the image size, a corresponding algorithm then calculates the actual path that the selected point or section traverses in the coordinate system, so that this can be displayed.

In addition to the above-described method, the invention is also directed to a method for determining movements of an organ or therapy region of a patient wherein a navigation system having a number of sensors is employed and a patient-specific coordinate system is defined with one or more sensors arranged at the patient at or in the region of location-invariant body parts. At least one sensor is placed at the moving organ or therapy region, the signal therefrom (generated or reflected) being acquired by the navigation system and the position thereof being continuously displayed at a monitor within the coordinate system also displayed at the monitor, or position data for this sensor are employed for determining at least a point characteristic of the motion path, which is displayed at the monitor within the coordinate system also displayed at the monitor.

In a further embodiment, the movement of at least one medical instrument to be guided with respect to the moving body organ or therapy region also can be acquired using at least one sensor, whose signal is acquired with the navigation system, arranged at the instrument. This movement of the instrument is likewise displayed in the coordinate system.

This version of the inventive method utilizes a sensor directly attached to the moving instrument or in the therapy region for determining the motion path. The complete path thereof can be displayed; alternatively, one or more characteristic points of the path can be calculated from the motion path and displayed, for example the two reversing points of a moving organ. In this case, the simultaneous acquisition of an image of the organ or of the therapy region can be foregone, since corresponding images are usually available from preliminary examinations of the organ or of the region. The physician, with reference to these images that are simultaneously presented can correlate the treatment region in the visualized image, for example a metastasis or the like, and the position of the organ as well as the movement thereof shown in the coordinate system, so that the physician can guide the medical instrument exactly to the target despite the lack of in situ presentation of the moving organ or region. Of course, it is possible to additionally acquire a real-time image of the moving organ or of the therapy region and display it at the same monitor or at another monitor, such as an ultrasound image. As a result, the physician can achieve an even better matching of the instrument movement to the motion cycle. In any case, monitoring as to whether the instrument has been guided exactly into the relevant region is presented on the basis of the registered image, namely when the tip of the instrument penetrates into the image plane, since then it becomes visible in the image.

As already described, a bone-proximate point on the skin of the patient should be selected as the location-invariant point. In order to allow subsequent examinations to again be able to establish the same coordinate system as existed in a prior examination, in accordance with the invention the selected point or points are first marked with an insertable cannula (needle) and subsequently an image documenting the position of the cannula is registered, such as an x-ray image, after which the points are durably marked by introducing a marking solution into the cannula and, the cannula is removed. As a result of the information provided on the basis of the versions of the inventive method, the operator or therapist can manually guide the instrument or instruments. The information determined according to the method, however, also makes it possible, based on the movement of the organ or of the therapy region acquired in the coordinate system, for a robot or the like to guide the medical instrument or instruments, and thus the movement of the instrument or instruments can be controlled with the navigation system identifying the spatial position of the medical instrument or instruments. The identified, spatial attitudinal or positional data according to this embodiment of the invention can be employed for the control of a robot or the like, which guides the instrument or instruments exactly into the target. The sizes of the individual instruments, for example the length of the needles, are known, so that the position of the tip of the needle can be exactly calculated dependent on the position of the respective sensor at the instrument, so that the spatial position of the needle can be identified and displayed with high precision. The determination and presentation of the instrument position in the case of manual guidance, of course also ensues correspondingly. Electromagnetic, optical or acoustic sensors can be inventively employed as the sensors. There is also the possibility of displaying the registered organ or the therapy region in segments at the monitor as the instrument successively proceeds through the segments.

In addition to being directed to the inventive method, the invention is also directed to a system for determining the movement of an organ or therapy region of a patient. The inventive system includes a navigation system having a number of sensors for defining a patient-specific coordinate system with one or more of the sensors arranged at the patient at or location-invariant body parts. An image pickup system registering an image of the moving organ or of the therapy region. A computer determines the attitude of the image plane—registered isochronically with the image pickup system—of a n image reproduced at a monitor of the moving organ or therapy region in the coordinate system on the basis of the position data of an essentially motionless sensor whose attitude within the coordinate system can be identified with the navigation system or on the basis of the spatial position of the image pickup system relative to the patient. A selection unit (which can be user-interactive) allows selection of at least one point or section of the moving organ or of the therapy region within the image. The motion-dependent path of the selected point or section is identified by the aforementioned computer or by another computer and, based thereon, at least one point characteristic of the motion path is identified and displayed at the aforementioned monitor, or at another monitor, within the coordinate system which is also displayed together with the attitude of the image plane.

The inventive system also can include at least one medical instrument provided with a sensor that can be acquired by the navigation system and that is to be guided with respect to the moving organ or therapy region. The position of the instrument can be identified by the navigation system and displayed at the monitor in the coordinate system.

A further inventive system includes a navigation system having a number of sensors which defines a patient-specific coordinate system with one or more of the sensors arranged at the patient at or in the region of location-invariant body parts, with at least one of the sensors being placed directly at the moving organ or the therapy region and the position thereof within the coordinate system being identified by the navigation system and displayed at a monitor.

This system also has at least one medical instrument provided with at least one sensor that can be acquired by the navigation system and that is to be guided with respect to the moving organ or the therapy region and whose position can be identified by the navigation system and displayed at the monitor in the coordinate system. This system serves for the implementation of the above-described, second version of the method, whereas the described system according to the first embodiment of the invention serves the purpose of implementing the method according to the first version of the invention.

In a further, embodiment of the invention the system includes at least one robot or the like that guides at least one medical instrument and that can be controlled dependent on the movement of the organ acquired in the coordinate system, the spatial position of the medical instrument or instruments being by the navigation system. Different computers can be employed for the implementation of the respective calculating or identification procedures as well as for the control of the robot or alternatively, only one central computer can be provided for these tasks.

DESCRIPTION OF THE PREFERRED EMBODIMENTS

Figure 1:
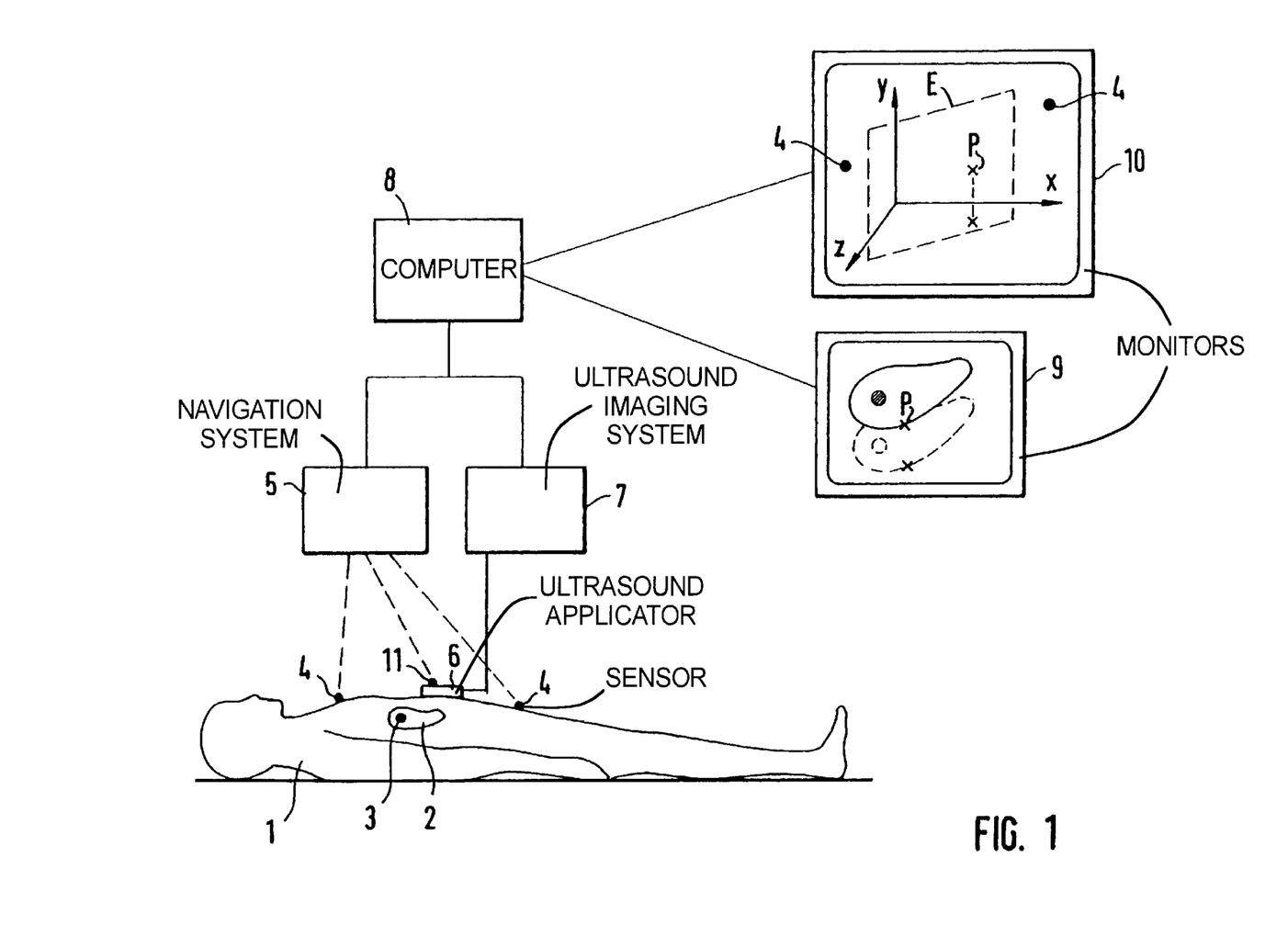
FIG. 1 is a schematic illustration of a first embodiment of an inventive apparatus, operating in accordance with a first embodiment of the inventive method.

FIG. 1 shows a patient 1 located on a support (not shown) whose liver 2 has a metastasis 3 to be treated. A number of sensors 4 are superficially applied to the patient 1; in the illustrated exemplary embodiment, a first sensor is in the region of the lower edge of the sternum, a second is located in the region of the upper iliac spur, and a further sensor can be disposed opposite at the other iliac spur. The respective positions of these two sensors are acquired with a navigation system 5. From this position data a patient-specific coordinate system is defined. Within this coordinate system the movement of the internal organ of the patient, which is moving due to respiration or pulsation and that is to be subjected to therapy, is acquired and determined (the liver 2 here). The positions of the x-axis, the y-axis and the z-axis of the coordinate system are determined on the basis of the positions of the sensors 4. At least one sensor 4 is required for defining the coordinate system; but a number of sensors 4 are useful for precision. The sensors 4 are arranged at location-invariant body regions, bone-proximate regions being suitable for this purpose. An ultrasound image of the liver 2 is registered with an ultrasound applicator 6 that is part of an ultrasound imaging system 7, with the image plane preferably proceeding essentially in the direction of the longitudinal axis of the liver 2. The image data registered with the ultrasound imaging system 7 are forwarded to a central computer 8 and are used to construct an ultrasound image which is displayed at a monitor 9. The movement of the liver 2 can be clearly seen therein, as shown in FIG. 1.

In order to then be able to acquire and display the movement of the liver 2 within the coordinate system, a point P at the organ is first selected at the monitor 9 by the operator or therapist, the lower liver edge in the illustrated example. This, for example, can ensue by using a touch screen monitor as the monitor 9. This point P is then tracked as to its movement and the motion path is determined with the computer 8. The presentation of this path ensues at a further monitor 10 at which the coordinate system within which the motion path is identified is likewise displayed, this being shown as an example In a Cartesian (x, y, z) coordinate system presentation. In addition to the coordinate axes, the two positions of the sensors 4 are also shown that serve as location-invariant points of reference for the movement of the organ or of the characteristic motion point. In order to be able to recognize the spatial direction of the motion path of the selected point within the coordinate system, another sensor 11 is provided at the ultrasound applicator 6 via which the attitude of the image plane E of the registered ultrasound image is identified. The image plane E is also displayed at the monitor 10, as indicated as an example In FIG. 1. The selected characteristic point P is then shown within the coordinate system and within the image plane E. The respective, motion-dependent extreme positions, i.e. the reversing points of the motion, are shown in the illustrated example. The organ, the liver 2 in this case, thus moves between these two points. In conjunction with the ultrasound image that he is shown, the operator or therapist can identify the momentary position of the liver on the basis of this presentation, and can also identify the position thereof in the patient-specific coordinate system.

To allow an operator or therapist to guide a medical instrument for treating the organ exactly thereto and, in the illustrated example, to the metastasis 3, exact knowledge of the organ motion is required, as is provided according to the method an system described with reference to FIG. 1.

Figure 2:
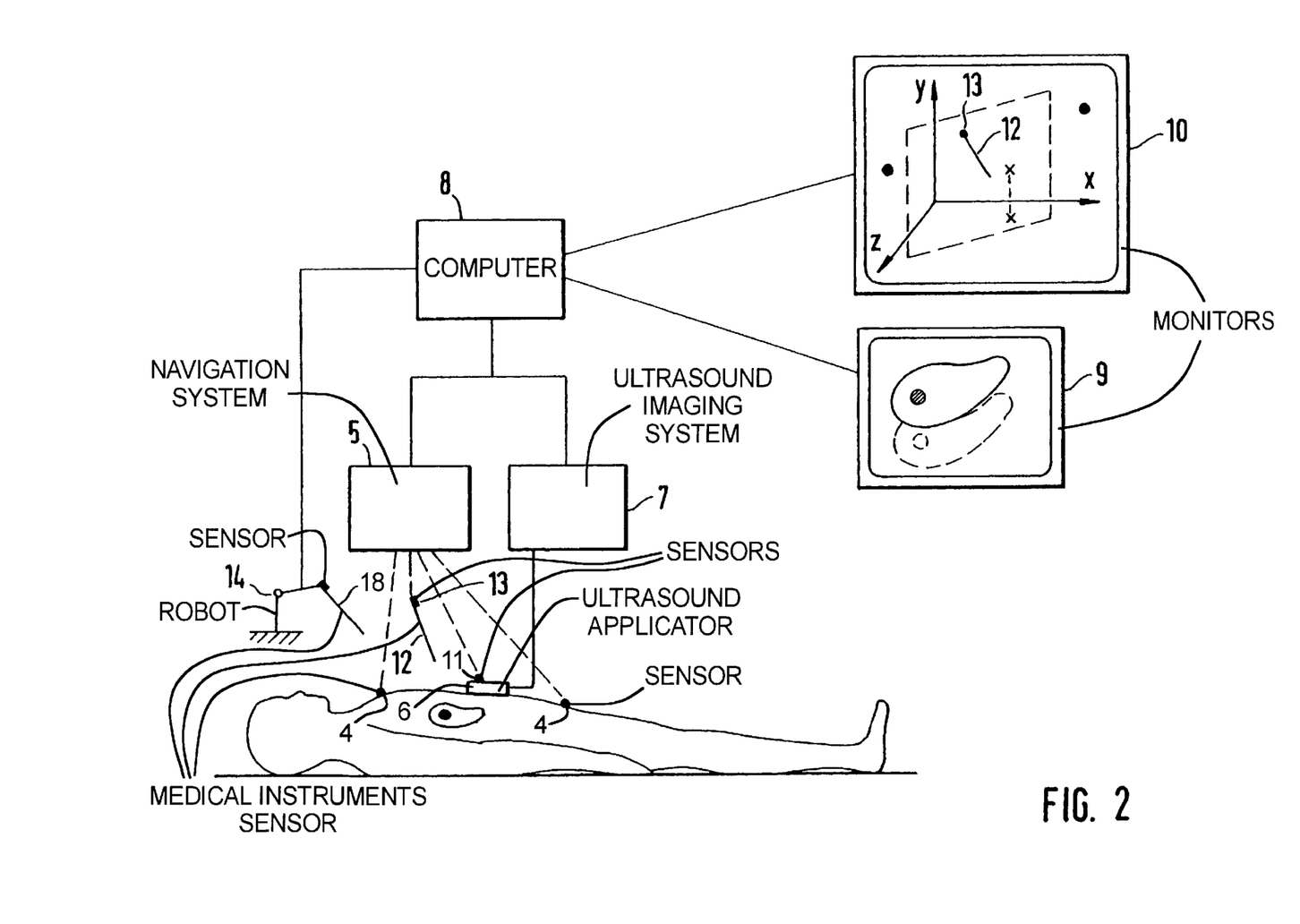
FIG. 2 is a schematic illustration of a second embodiment of an inventive apparatus, operating in accordance with a second embodiment of the inventive method.

Additionally, the spatial attitude of the medical instrument must be identified in the patient-specific coordinate system so that the operator or therapist can see what spatial position the instrument is assuming at the moment relative to the moving organ, and in what direction this instrument must be guided. To this end, a sensor 13 that is likewise acquired with the navigation system 5 is provided at the medical instrument 12, a needle in the illustrated example. The computer 8 is then able to determine the spatial attitude of the instrument 12 in the coordinate system and to display this information at the monitor 10. The attitude of the tip of the instrument that is to be conducted to the metastasis 3 is thereby relevant to the operator, for which reason the computer 8, for example, displays an image the instrument 12 over its entire length, which is known to the computer 8. With reference to the presentation at the monitor 10, the operator can then exactly recognize the spatial position of the instrument 12 within the coordinate system and with reference to the image plane E, so that it is possible to conduct the tip of the instrument 12 exactly into the target region in conjunction with the display at the monitor 9. The final check ultimately ensues via the fact that the tip 12—when it has arrived in the region of the metastasis 3—is usually visible in the ultrasound image at the monitor 9, since it is then located in the image plane E. In this way, the operator or therapist can manually guide the instrument 12.

Based on the knowledge of the movement of the organ and the acquisition thereof within the coordinate system, however, it is also possible to control the movement of a robot 14 or the like at which a medical instrument, for example a needle, is held, i.e. the instrument 15 (with a sensor 18) is not manually guided in this case but is automatically guided with the robot 14. In the illustrated example, the control of the robot 14 ensues by the computer 8 from which the robot 14 obtains the corresponding control information in view of the respective movements in the x, y and z directions as well as the spatial angles α,β and y with respect to the spatial axes. In this case as well, the spatial attitude of the instrument 15 can be mixed into the image at the monitor 10, even though this is not absolutely necessary since the instrument guidance is automatically controlled. A number of instruments, separately controllable in terms of their motion can also be arranged at the robot 14.

Figure 3:
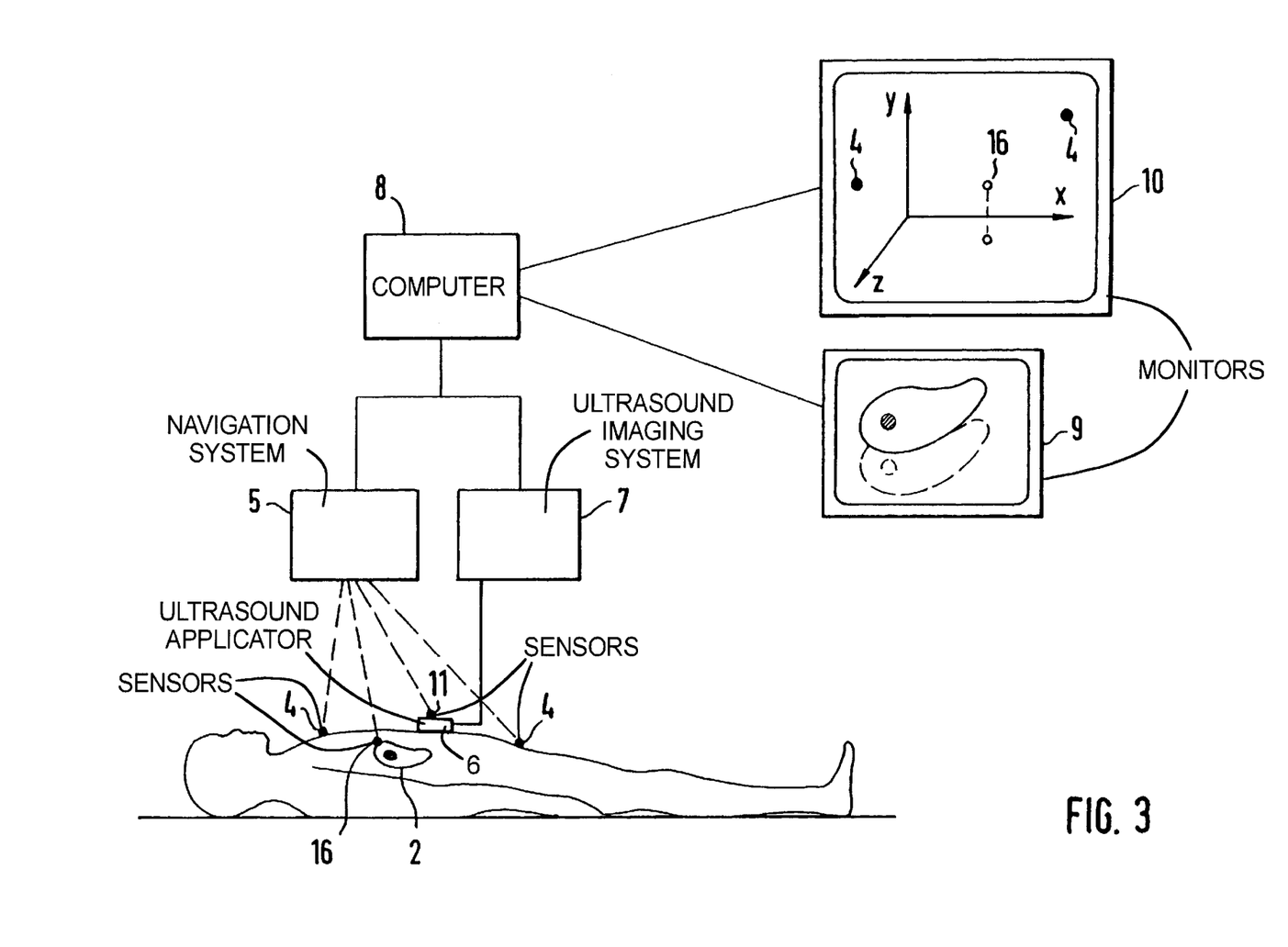
FIG. 3 is a schematic illustration of a third embodiment of an inventive apparatus, operating in accordance with a third embodiment of the inventive method.

FIG. 3 shows a further possibility for acquiring the organ movement. In addition to the sensors 4 also employed here, a sensor 16 directly applied to the outside of the liver 2 is utilized here, this having been applied thereto within the framework of a minor operative intervention. Since this sensor 16 moves directly together with the liver 2, an acquisition of an ultrasound image of the liver 2 is basically not required. The acquisition of the movement of the sensor 16 with the navigation system 5 makes it immediately possible for the computer 8 to display the motion path of the sensor 16 within the coordinate system at the monitor 10. The operator or therapist can already guide the instrument (not shown in FIG. 3) relative to the liver 2 on the basis of this knowledge, insofar as corresponding exposures of the liver 2 and thus of the position of the metastasis, are available to the operator on the basis of preliminary examinations.

Insofar as the operator can correlate the metastasis position with the position and movement of the sensor 16 on the basis of these earlier exposures, it is possible for the operator to guide the instrument into the target region. As FIG. 3 shows, it is nonetheless possible and meaningful to undertake an in situ exposure with the ultrasound system 7. Even though it is not shown in FIG. 3, it is possible to display the attitude of the image plane that is identifiable by the acquisition of the sensor 11 at the monitor 10. Since the acquisition of the medical instrument ensues in the manual as well as in the automatic case in conformity with the exemplary embodiment described with reference to FIG. 2, further discussion thereof is not required at this point.

Figure 4:
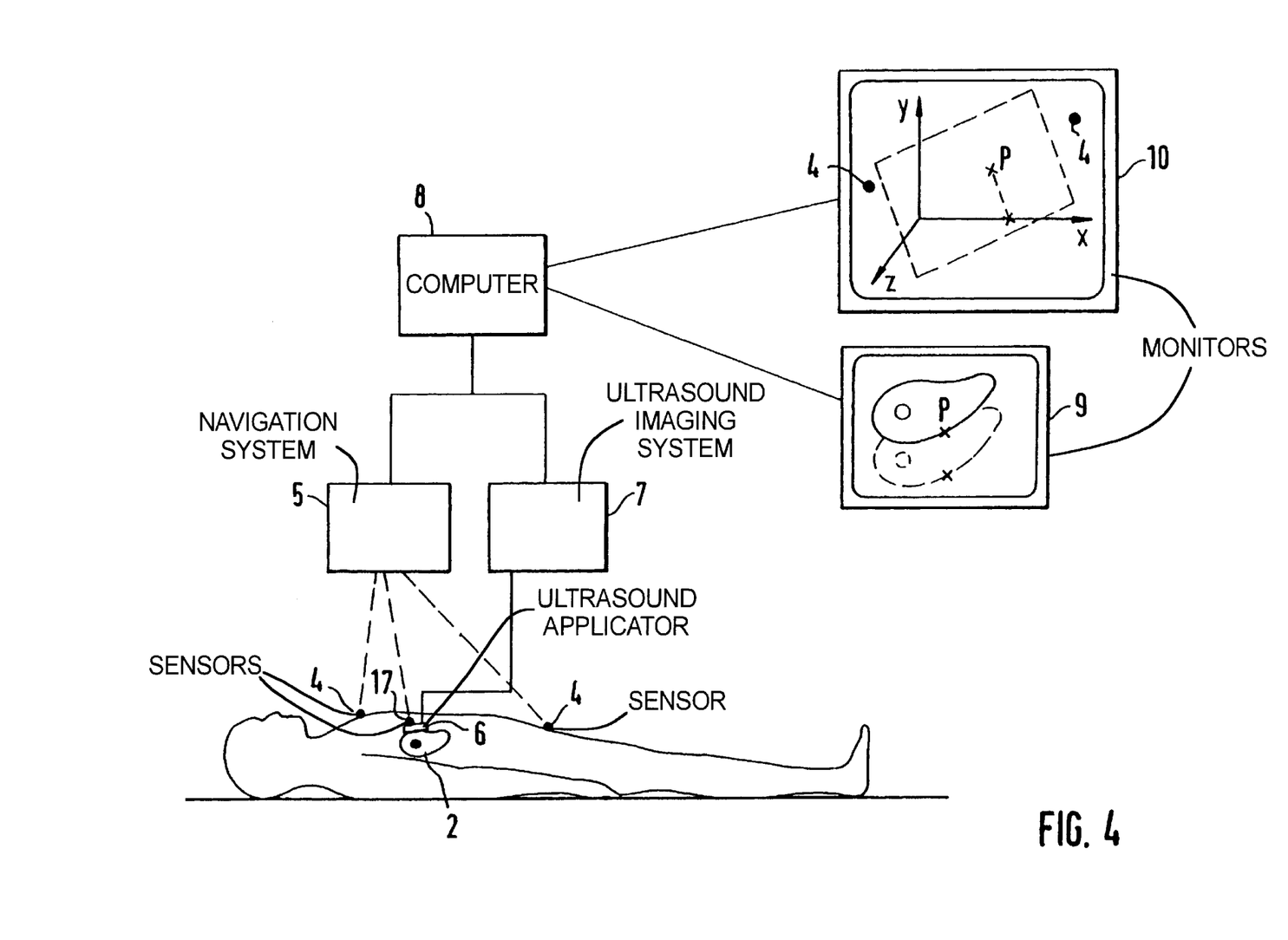
FIG. 4 is a schematic illustration of a fourth embodiment of an inventive apparatus, operating in accordance with a fourth embodiment of the inventive method.

FIG. 4 shows a third possibility of acquiring the organ movement. This possibility fundamentally corresponds to the embodiment according to FIG. 1; however, the ultrasound applicator 17 of the ultrasound system 7 in this exemplary embodiment is applied directly on the liver 2 and not on the surface of the abdominal wall as in the example of FIG. 1. To this end, the ultrasound applicator 17 is pushed into the abdominal cavity via a small body opening. The applicator 17 does not move together with the liver 2 but is stationary relative thereto, i.e. the sensor 18 (as well as the sensor 11 in FIG. 1) is at rest relative to the moving liver 2. The determination of the motion path ensues in the same way as described with reference to FIG. 1. This is also true with respect to the acquisition of the instruments (likewise not shown here) that are to be guided manually or by robot; this ensues in the same way as described with reference to FIG. 2.

The described image pickup system can alternatively be an x-ray system. In this case, the determination of the image plane ensues on the basis of the alignment of the central ray between the x-ray tube and the x-ray receiver with respect to the patient relative to the patient-specific coordinate system that is also defined with corresponding sensors in this case. The identification of the spatial attitude of the sensors which ensue with the navigation system, can be undertaken in the central computer 8 in a computing module for the implementation of these calculating operations. Of course, it is also possible to employ a separate computer allocated to the navigation system and the image pick-up system instead of the central computer 8.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for determining movement of a site in a patient, comprising the steps of:

disposing one or more sensors respectively at location-invariant body parts of a patient;

obtaining respective signals from said sensors and from said signals defining a patient-specific coordinate system, and displaying said patient-specific coordinate system in a first display presentation of a display monitor system;

obtaining a substantially real-time image, in an image plane, of a region of said patient containing a moving site and displaying said image in a second display presentation of said display monitor system;

identifying an orientation of said image plane in said patient-specific coordinate system and displaying a representation of said image plane with said orientation in said patient-specific coordinate system in said first display presentation; and defining at least a point in said second display presentation which exhibits a motion path dependent on movement of said movement site, and displaying at least one characteristic point of said motion path in said image plane in said first display presentation.

2. A method as claimed in claim 1 wherein the step of identifying said orientation of said image plane in said patient-specific coordinate system comprises identifying a position of at least one of said sensors which is substantially motionless relative to said moving site and using position data from said at least one sensor to identify said orientation of said image plane.

3. A method as claimed in claim 1 wherein the step of obtaining said substantially real-time image comprises obtaining said substantially real-time image with an image registration system having a spatial position, and wherein the step of identifying said orientation of said image plane in said patient-specific coordinate system comprises identifying said spatial position of said image registration system in said patient-specific coordinate system.

4. A method as claimed in claim 1 wherein said display monitor system comprises a single monitor, and displaying said first display presentation and said second display presentation on said single monitor.

5. A method as claimed in claim 1 wherein said display monitor system comprises a first monitor and a second monitor, and displaying said first display presentation on said first monitor and displaying said second display presentation on said second monitor.

6. A method as claimed in claim 1 comprising the additional steps of:
providing a medical instrument to be guided relative to said moving site;
mounting a sensor at said medical instrument; and
obtaining a signal from said sensor mounted at said medical instrument and from said signal identifying a position of said medical instrument and displaying said position of said medical instrument in said patient-specific coordinate system in said first display presentation.

7. A method as claimed in claim 6 comprising the additional steps of:
mounting said medical instrument in a robot; and
automatically operating said robot to guide said medical instrument relative to said moving site dependent on information contained in said first display presentation.

8. A method as claimed in claim 1 wherein the step of obtaining a substantially real-time image comprises obtaining a substantially real-time image from the group consisting of ultrasound images and x-ray images.

9. A method as claimed in claim 1 comprising obtaining an ultrasound image, using an ultrasound applicator, as said substantially real-time image, and mounting a sensor at said ultrasound applicator and using said sensor mounted at said ultrasound applicator as a sensor which is substantially motionless relative to said moving site and using position data from said sensor mounted at said ultrasound applicator to identify said orientation of said image plane.

10. A method as claimed in claim 9 comprising applying said ultrasound applicator superficially at said patient.

11. A method as claimed in claim 9 comprising introducing said ultrasound applicator into said patient.

12. A method as claimed in claim 1 wherein said moving site is contained within an organ in said patient, said organ having a longitudinal axis, and wherein the step of obtaining said substantially real-time image comprises obtaining a substantially real-time image in an image plane proceeding substantially along said longitudinal axis of said organ.

13. A method as claimed in claim 1 wherein said moving site is contained within an therapy region in said patient, said therapy region having a longitudinal axis, and wherein the step of obtaining said substantially real-time image comprises obtaining a substantially real-time image in an image plane proceeding substantially along said longitudinal axis of said therapy region.

14. A method as claimed in claim 1 wherein the step of defining at least a point in said second display presentation comprises touching said second display presentation at a location to define said point, and registering said location at which said second display presentation is touched.

15. A method as claimed in claim 1 comprising selecting said sensors in said plurality of sensors from the group consisting of electromagnetic sensors, optical sensor, and acoustic sensors.

16. A method as claimed in claim 1 comprising displaying said real-time image in successive segments in said second display presentation.

17. A method as claimed in claim 1 comprising placing one of said sensors at above-proximate locations of said patient.

18. A method for determining movement of a site in a patient, comprising the steps of:
disposing a plurality of sensors respectively at location-invariant body parts of a patient;
obtaining respective signals from said sensors and from said signals defining a patient-specific coordinate system and displaying said patient-specific coordinate system;
placing at least one further sensor at a moving site in said patient, said further sensor placed at said moving site producing a sensor signal dependent on movement of said moving site; and
from said signal from said further sensor placed at said moving site, displaying at least one point in said display of said patient-specific coordinate system which is characteristic of a motion path of said moving site.

19. A method as claimed in claim 18 comprising continuously displaying, in said display of said patient-specific coordinate system, the position of said further sensor placed at said moving site as said representation of said movement of said moving site.

20. A method as claimed in claim 18 comprising obtaining position data from said signal from said further sensor placed at said moving site and, from said position data, calculating said motion path, and from the calculated motion path selecting and displaying said at least one point which is characteristic of said motion path.

21. A method as claimed in claim 18 comprising the additional steps of:
providing a medical instrument to be guided relative to said moving site;
mounting an additional sensor at said medical instrument; and
obtaining a signal from said additional sensor mounted at said medical instrument and from said signal identifying a position of said medical instrument and displaying said position of said medical instrument in said patient-specific coordinate system in said first display presentation.

22. A method as claimed in claim 21 comprising the additional steps of:
mounting said medical instrument in a robot; and
automatically operating said robot to guide said medical instrument relative to said moving site dependent on information contained in said first display presentation.

23. A method as claimed in claim 18 comprising the additional step of obtaining a substantially real-time image of a region of said patient containing said moving site, from the group consisting of ultrasound images and x-ray images.

24. A method as claimed in claim 23 wherein said moving site is contained within an organ in said patient, said organ having a longitudinal axis, and wherein the step of obtaining said substantially real-time image comprises obtaining a substantially real-time image in an image plane proceeding substantially along said longitudinal axis of said organ.

25. A method as claimed in claim 23 wherein said moving site is contained within an therapy region in said patient, said therapy region having a longitudinal axis, and wherein the step of obtaining said substantially real-time image comprises obtaining a substantially real-time image in an image plane proceeding substantially along said longitudinal axis of said therapy region.

26. A method as claimed in claim 18 wherein the step of placing at least one further sensor at a moving site comprises introducing a cannula into said patient to said moving site, producing an image of a region of said patient containing said cannula, and durably marking a point at said moving site with a marking solution supplied through said cannula, and removing said cannula from said patient.

27. A method as claimed in claim 18 comprising selecting said sensors in said plurality of sensors from the group consisting of electromagnetic sensors, optical sensors, and acoustic sensors, and selecting said at least one further sensor from the group consisting of electromagnetic sensors, optical sensors, and acoustic sensors.

28. An apparatus method for determining movement of a site in a patient, comprising:
one or more sensors adapted for placement respectively at location-invariant body parts of a patient;
means for obtaining respective signals from said sensors and from said signals defining a patient-specific coordinate system;
a display monitor system for displaying said patient-specific coordinate system in a first display presentation;
an image registration system for obtaining a substantially real-time image, in an image plane, of a region of said patient containing a moving site and connected to said display monitor system for displaying said image in a second display presentation of said display monitor system;
means for identifying an orientation of said image plane in said patient-specific coordinate system and for causing display of a representation of said image plane with said orientation in said patient-specific coordinate system in said first display presentation; and
means for defining at least a point in said second display presentation which exhibits a motion path dependent on movement of said movement site, and for causing display of at least one characteristic point of said motion path in said image plane in said first display presentation.

29. An apparatus as claimed in claim 28 wherein said means for identifying said orientation of said image plane in said patient-specific coordinate system comprises means for identifying a position of at least one of said sensors which is substantially motionless relative to said moving site and using position data from said at least one sensor to identify said orientation of said image plane.

30. An apparatus as claimed in claim 28 wherein said image registration system has a spatial position, and wherein said means identifying said orientation of said image plane in said patient-specific coordinate system identifies said spatial position of said image registration system in said patient-specific coordinate system.

31. An apparatus as claimed in claim 28 wherein said display monitor system comprises a single monitor, and displays said first display presentation and said second display presentation on said single monitor.

32. An apparatus as claimed in claim 28 wherein said display monitor system comprises a first monitor and a second monitor, and displays said first display presentation on said first monitor and displays said second display presentation on said second monitor.

33. An apparatus as claimed in claim 28 further comprising:
a medical instrument to be guided relative to said moving site;
an additional sensor mounted at said medical instrument;
wherein said means for obtaining respective signals also obtains a signal from said additional sensor mounted at said medical instrument; and
means for identifying a position of said medical instrument from said signal and for causing display of said position of said medical instrument in said patient-specific coordinate system in said first display presentation.

34. An apparatus as claimed in claim 33 further comprising:
a robot in which said medical instrument is mounted; and
means for automatically operating said robot to guide said medical instrument relative to said moving site dependent on information contained in said first display presentation.

35. An apparatus as claimed in claim 28 wherein said image registration system comprises a system from the group consisting of ultrasound imaging systems and x-ray imaging systems.

36. An apparatus as claimed in claim 28 wherein said image registration system comprises an ultrasound imaging system, having an ultrasound applicator, and wherein one of said sensor is mounted at said ultrasound applicator as a sensor which is substantially motionless relative to said moving site, and wherein said means for identifying said orientation of said image plane identifies said orientation of said image plane using a signal from said sensor mounted at said ultrasound applicator.

37. An apparatus as claimed in claim 36 wherein said ultrasound applicator is adopted for superficial application at said patient.

38. An apparatus as claimed in claim 36 wherein said ultrasound applicator is adopted for introduction into said patient.

39. An apparatus as claimed in claim 28 wherein said moving site is contained within an organ in said patient, said organ having a longitudinal axis, and wherein said image registration system obtains said substantially real-time image in an image plane proceeding substantially along said longitudinal axis of said organ.

40. An apparatus as claimed in claim 28 wherein said moving site is contained within an therapy region in said patient, said therapy region having a longitudinal axis, and wherein said image registration system obtains said substantially real-time image in an image plane proceeding substantially along said longitudinal axis of said therapy region.

41. An apparatus as claimed in claim 28 wherein display monitor system comprises a touch-sensitive screen on which said second display presentation is displayed, and wherein said point is defined by touching said screen at a selected location.

42. An apparatus as claimed in claim 28 wherein said display monitor system comprises a light pen responsive screen on which said second display presentation is displayed, and a light pen, and wherein said point is defined by touching said screen with said light pen at a selected location.

43. An apparatus for determining movement of a site in a patient, comprising the steps of:

one or more sensors adapted for placement respectively at location-invariant body parts of a patient;

means for obtaining respective signals from said sensors and from said signals defining a patient-specific coordinate system;

a monitor for displaying said patient-specific coordinate system;

at least one further sensor at a moving site in said patient, said sensor placed at said moving site producing a sensor signal dependent on movement of said site; and means for receiving said signal from said further sensor placed at said moving site, and for causing display of at least one point in said display of said patient-specific coordinate system at said monitor which is characteristic of a motion path of said moving site.

44. An apparatus as claimed in claim 43 comprising means for continuously displaying, in said display of said patient-specific coordinate system on said monitor, the position of said further sensor placed at said moving site as said representation of said movement of said moving site.

45. An apparatus as claimed in claim 43 comprising means for obtaining position data from said signal from said further sensor placed at said moving site and, from said position data and for calculating said motion path, and from the calculated motion path selecting and displaying said at least one point which is characteristic of said motion path.

46. An apparatus as claimed in claim 43 further comprising:

a medical instrument to be guided relative to said moving site;

an additional sensor mounted at said medical instrument;

wherein said means for obtaining respective signals also obtains a signal from said additional sensor mounted at said medical instrument; and means for identifying a position of said medical instrument from said signal and for causing display of said position of said medical instrument in said patient-specific coordinate system in said first display presentation.

47. An apparatus as claimed in claim 46 further comprising:

a robot in which said medical instrument is mounted; and means for automatically operating said robot to guide said medical instrument relative to said moving site dependent on information contained in said first display presentation.

48. An apparatus as claimed in claim 43 further comprising an image registration system for obtaining a substantially real-time image of a region of said patient containing said moving site, selected from the group of systems comprising ultrasound imaging systems and x-ray imaging systems.

49. An apparatus as claimed in claim 48 wherein said moving site is contained within an organ in said patient, said organ having a longitudinal axis, and wherein said image registration system obtains said substantially real-time image in an image plane proceeding substantially along said longitudinal axis of said organ.

50. An apparatus as claimed in claim 48 wherein said moving site is contained within an therapy region in said patient, said therapy region having a longitudinal axis, and wherein said image registration system obtains said substantially real-time image in an image plane proceeding substantially along said longitudinal axis of said therapy region.

51. An apparatus as claimed in claim 48 comprising a cannula introducible into said patient for marking said moving site with a marking solution supplied through said cannula, to form said sensor at said moving site, and wherein said image registration system obtains an image of said cannula in said patient to guide said cannula.

* * * * *